United States Patent [19]

Davidson et al.

[11] Patent Number: 5,537,876
[45] Date of Patent: Jul. 23, 1996

[54] APPARATUS AND METHOD FOR NONDESTRUCTIVE EVALUATION OF BUTT WELDS

[76] Inventors: Paul K. Davidson, 1400 Lafayette, NE., Albuquerque, N.M. 87106; George A. Alers, 1209 Harrison Ct., Boulder, Colo. 80303; Robert B. Thompson, 3212 Kingman, Ames, Iowa 50011; Leigh R. Burns, Jr., 104 Kenneth, Troy, Ill. 62294

[21] Appl. No.: 285,391

[22] Filed: Aug. 2, 1994

[51] Int. Cl.⁶ .................................................. G01N 29/10
[52] U.S. Cl. .............................. 73/624; 73/643; 228/56.5; 228/104
[58] Field of Search .............................. 73/643, 622, 624, 73/634; 228/56.5, 104

[56] References Cited

U.S. PATENT DOCUMENTS 5,439,157  8/1995  Grier et al. ............................ 228/56.5

*Primary Examiner*—John E. Chapman
*Attorney, Agent, or Firm*—Samuel M. Freund

[57] ABSTRACT

Apparatus and method for nondestructive evaluation of butt welds. The present invention in its broadest form includes an apparatus and method for detecting flaws in butt welds in steel sheets using horizontal shear ultrasonic waves generated on the surface thereof. Observation of reflected waves having amplitude greater than a chosen value signals the presence of significant flaw. To achieve this objective, the present apparatus detects only reflected horizontal shear waves; other modes are electronically removed using bandpass filters, since they occur at different frequencies. The invention may therefore be used in the presence of surface structures such as clamps and the like, and in the presence of surface nonuniformities in the vicinity of the weld, thereby permitting on-line flaw detection steel mill environment without interfering with the line output. The ultrasonic waves are generated and received by a pair of electromagnetic acoustical transducers having magnetic fields which are oriented 40–65 degrees from the direction of the transmitted and received waves.

9 Claims, 7 Drawing Sheets

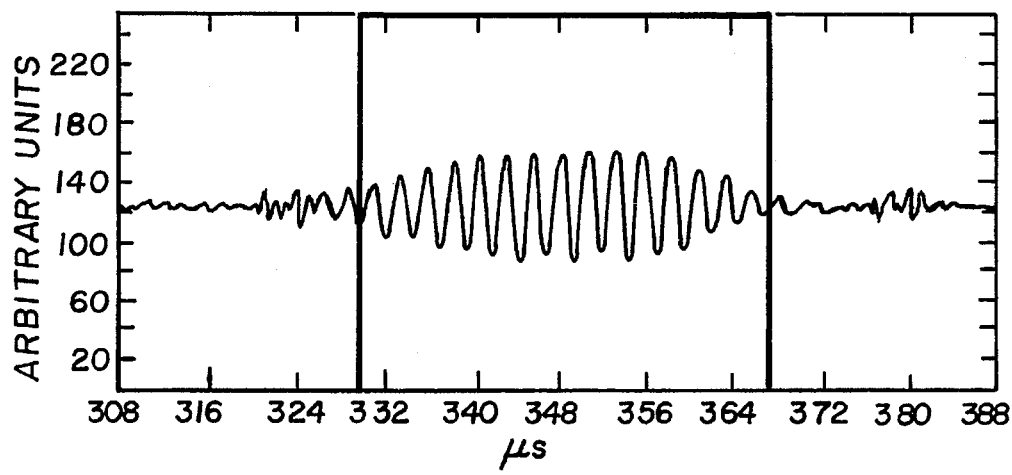
FIG. 9.
FIG. 10a.
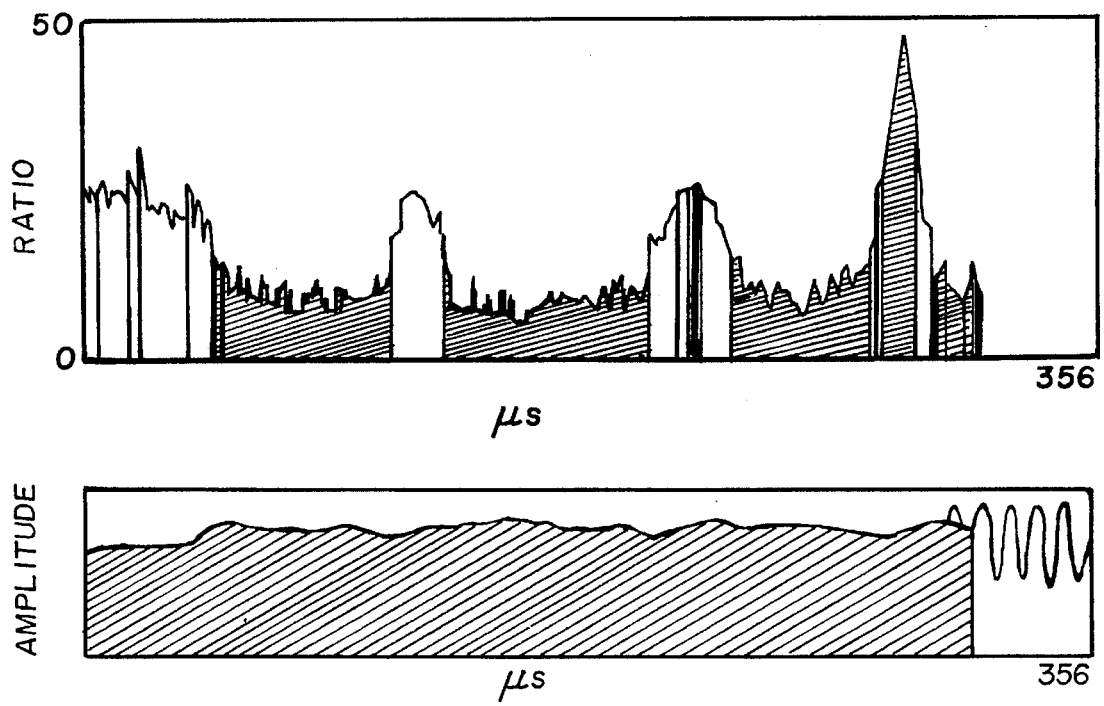
FIG. 10b.

APPARATUS AND METHOD FOR NONDESTRUCTIVE EVALUATION OF BUTT WELDS

BACKGROUND OF THE INVENTION

The present invention relates generally to nondestructive testing of welds and, more particularly, to an apparatus and method using electromagnetic acoustic transducers for generating and directing horizontal waves in welded steel sheet in the direction of a butt weld, and for detecting reflected waves from weld imperfections without interference from surface irregularities and external objects.

Weld breakage lengthy coils fabricated from steel sheet results in a significant loss in production output, with a resulting loss in time and money to the steel industry. Typical industry breakage rates are between 0.5 and 1% of all welds. Generally, these welds break during the cold reduction process where the coils are cold rolled to a product having a desired gauge.

A common mill operation is where the tail of one coil is flash but t-welded to the head of an other in order that sufficient length for efficient processing and/or for a particular application is achieved. The completed weld is then clamped under a flash trimmer which is used to trim weld debris so that the sheet appears continuous. The process line halted for the welding and trimming processes, after which the larger coil is further processed. When in motion, the steel sheet travels at about 30 mph until the end of the coil approaches the welding apparatus, and another coil is welded on. There are numerous nondestructive testing techniques available to the steel industry to characterize welds. For example, measurements employing eddy currents, magnetic flux, magnetic resonance, and traditional ultrasonic methods are adequate under certain circumstances, but all of these techniques have limited applicability under constraints found in steel mills. That is, inspection procedures must not impact the normal operation of a mill's production line.

Piezoelectric-driven ultrasonic transducers have been utilized for weld inspection. See, for example, U.S. Pat. No. 3,868,847, for "System And Apparatus For Inspecting Elongated Welds," which issued to Walter A. Gunkel on Mar. 4, 1975, for a discussion of the use of these devices for weld investigation. The apparatus described therein, however, would not be useful for the high speed buttwelding applications in steel mills, since water is required to provide acoustic fluid coupling and a bearing surface for each of the transducers employed. Moreover, the apparatus must be accurately positioned over the weld bead in order to practice the Gunkel invention. This requires the additional step of indexing the steel sheet such that the apparatus might be attached. U.S. Pat. No. 4,395,913 for "Broadband Electromagnetic Acoustic Transducers," which issued to William E. Peterson on Aug. 2, 1983 more generally discusses the problems With contact procedures.

Eddy current methods are restricted to a thin skin depth of the material under investigation, and similarly to magnetic flux and resonance techniques are more suitable for crack detection in surfaces than for investigation of weld characteristics. U.S. Pat. No. 4,644,272, for "Hot Annealed Weld Inspection," which issued to Wilbert J. Janos on Feb. 17, 1987 discusses an eddy current system for hot annealed weld inspection.

The use of the Shear Horizontal (SH) mode in ultrasonic waves for inspecting weld defects is known. That is, the use of such waves is preferred for characterizing defects inside symmetric discontinuities, since many other wave modes are reflected by the weld itself, thereby generating significant background noise. See, for example, U.S. Pat. No. 4,289,030, for "Nondestructive Testing Utilizing Horizontally Polarized Shear Waves", which issued to George A. Alers et al. on Sep. 15, 1981. Moreover, in order for the welding flash to be removed, the sheet steel must be clamped in place. Since the flash knife clamps hold the steel sheet with several thousand psi of pressure, principally the SH ultrasonic waves can pass under the knife, reflect from the weld and return to a detector without being impacted by the presence of the clamps.

Electromagnetic Acoustical Transducers (EMATs) can generate SH waves in steel, do not require direct contact with the workpiece, and can be pulsed at rates which permit rapid scanning of welds. Unlike piezoelectric ultrasonic techniques and eddy current technology, EMATs require little tuning once initial setup is completed. Therefore, EMATs provide an adequate solution to the mill tradeoff between time required for weld inspection and lost production time. The design of EMAT transducers for various purposes including weld inspection is well documented. See, for example, "The Design And Use Of Electromagnetic Acoustic Wave Transducers (EMATs)" by B. W. Maxfield and C. M. Fortunko, Materials Evaluation, 41, 1399 (1983), "Evaluating EMAT Designs For Selected Applications," by B. W. Maxfield, A. Kuramoto, and J. K. Hulbert, Materials Evaluation 45, 1166 (1987), "EMAT Designs For Special Applications", G. A. Alers and L. R. Burns, Materials Evaluation 45, 1184 (1987), and "Ultrasonic Nondestructive Evaluations Of Butt Welds Using Electromagnetic-Acoustic Transducers," by C. M. Fortunko and R. E. Schramm, Welding Journal, pages 39–46 (February, 1982). What generally separates EMAT technologies is 1. the orientation of the EMAT wires relative to the magnetic field, 2. the plane of the EMAT relative to the plane of the magnetic flux lines, and 3. the type of magnet used.

Parallel field SH wave EMAT technology is described in U.S. Pat. No. 4,295,214, for "Ultrasonic Shear Wave Transducer," which issued to Robert B. Thompson on Oct. 13, 1981, and in U.S. Pat. No. 4,100,809, for "Method For Excitation And Reception Of Ultrasonic Plate Waves In Workpieces And Devices For Realizing Same," which issued to Vladimir Timofeevich Bobrov et al. on Jul. 18, 1978. Because of the EMAT design employed, large magnet fields (1200 to 1500 Oersteds) must be generated in the sheet steel. Bobrov et al. discloses EMAT utilization at the "Magic Angle;" that is, where the EMAT generates Horizontal Shear waves in the material of interest in a direction neither perpendicular nor parallel to the direction of the magnetizing field generated by a magnet parallel to the surface of the material for providing increase coupling between the material of interest and the high-frequency electromagnetic field (See, for example, *Ultrasonic Testing Of Materials*, by J. Kraut Kramer and H. Kraut Kramer, 4th Ed. Springer Verlag (1990).). Bobrov et al. employ EMATs to investigate welds. Longitudinal and transverse (SH) plate waves, generated by the EMAT same and subsequently reflected from flaws in the material, are time analyzed in order to provide information concerning the nature of the flaw. In Column 20, lines 44–49, the statement is made that when both excitation frequencies are simultaneously introduced into the material, the longitudinal and transverse plate waves reflected from the flaw cannot be separated by time gating. This statement is important for analyzing butt welds, since EMAT use at the "Magic Angle" generates more than one plate mode. Although one may optimize the amount of one mode over the others depending on the angle employed, reflected signals from other sources, such as surface irregularities or the presence of trim knife clamps as described above, will interfere with signals produced by flaws in the weld. It should be mentioned that the "Magic Angle" is employed since the coupling between the EMAT and a ferromagnetic material is substantially improved away from 90°, even though additional modes are generated. Moreover, in lines 50–54 of Column 20, Bobrov et al. conclude that for investigation of welded seams, only focused longitudinal plate waves should be employed.

U.S. Pat. No. 4,295,214, supra, discusses the use of electromagnetic acoustic transducers for generating horizontal shear waves for the purpose of weld inspection; the times of arrival of the generated and reflected waves being correlated to determine the circumferential position of the flaw. This patent, also describes the use of a static magnetic field parallel to the surface of the material under investigation, and perpendicular to the generated wave.

Accordingly, an object of the present invention is to provide an apparatus for detecting the presence of flaws in butt welds.

Another object of the invention is to provide an apparatus for detecting the presence of flaws in butt welds in steel sheet in the presence of trim knife clamps, with negligible impact on steel mill production.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus for non-destructive detection of flaws in butt-welded steel sheet includes an electromagnetic acoustical transducer for generating horizontal shear mode ultrasonic waves in the steel sheet approximately perpendicular to and on one side of the weld; a pulsed or dc magnet for generating a magnetic field parallel to the surface of the sheet and at between 40° and 65° to the direct of the horizontal shear mode ultrasonic waves in the vicinity of the generation thereof by the generating transducer an electromagnetic acoustical transducer for receiving ultrasonic waves in the steel sheet reflected by the weld and for generating an electrical signal responsive thereto, the receiving transducer being located on the same side of the weld as the generating transducer, corresponding features of the two transducers forming a line perpendicular to the weld; a magnet for generating a magnetic field parallel to the surface of the sheet and at between 40° and 65° to the direction of received horizontal shear mode ultrasonic waves the vicinity of the reception thereof by the receiving transducer; means for moving the generating transducer and the receiving transducer across the surface of the steel sheet in a line parallel to the weld; a signal analyzer for receiving the electrical signal generated by the receiving transducer and comparing the received signal with that for a weld with acceptable faults; and means for removing signals from acoustical wave modes in the steel sheet reflected from the weld other than horizontal shear mode acoustical waves from the electrical signals generated by the receiving transducer before they reach the signal analyzer.

Preferably, the means for removing unwanted signals from the output of the receiving transducer before reaching the signal analyzer includes a band-pass electrical filter chosen to pass electrical signals having frequencies associated with horizontal shear mode acoustical waves.

It is also preferred that the signal analyzer is time-gated and blanked in order to prevent other modes than the horizontal shear mode acoustical waves generated by the generating transducer and reflected from the weld from contributing to electrical signals from the receiving transducer generated in response to horizontal shear mode acoustical waves reflected from the weld.

Preferably also, edge locating means are provided for locating each edge of the steel sheet in the vicinity of the line of traverse of the two transducers across the steel sheet.

It is preferred that the receiving transducer is disposed between the weld and the generating transducer.

In a further aspect of the present invention, accordance with its objects and purposes, the method for detecting flaws in butt-welded steel sheet includes the steps of generating horizontal shear mode ultrasonic waves in the steel sheet approximately perpendicular to and on one side of the weld; generating a magnetic field parallel to the surface of the sheet and at between 40° and 65° to the direction of the horizontal shear mode ultrasonic waves in the vicinity of the generation thereof; receiving ultrasonic waves in the steel sheet reflected by the weld and generating an electrical signal responsive thereto on the same side of the weld as the waves are generated, there being a line formed by the received reflected waves and the generated waves approximately perpendicular to the weld; generating a magnetic field parallel to the surface of the sheet and at between 40° and 65° to the direction of the received horizontal shear mode ultrasonic waves; moving the line of the generated ultrasonic waves across the surface of the steel sheet perpendicular to the weld; removing signals from acoustical wave modes in the steel sheet reflected from the weld other than horizontal shear mode acoustical waves; and comparing the generated electrical signal with that for a weld with acceptable faults.

It is preferred that the step of removing signals from acoustical wave modes other than horizontal shear mode acoustical waves is accomplished using a band-pass electrical filter chosen to pass electrical signals having frequencies associated with horizontal shear mode acoustical waves from the generated electrical signal.

Preferably, the step of time-gating the generated electrical signal in order to prevent other modes than the horizontal shear mode acoustical waves reflected from the weld from contributing to the generated electrical signal, is included.

Benefits and advantages of the present invention include rapid and definitive flaw detection in butt welds in steel sheets having structures on the surface thereof in the vicinity of the weld, and in adverse environments, without significant interference with steel mill operations.

BRIEF DESCRIPTION OF THE DRAWINGS

The accompanying drawings, which are incorporated in and form a part of the specification, illustrate general embodiments of the present invention and, together with the description, serve to explain the principles of the invention.

FIG. 9 illustrates the received ultrasonic signal for a calibration experiment.

FIGS. 10a and 10b illustrates the received ultrasonic signal for a weld in which several flaws have been purposefully introduced.

DETAILED DESCRIPTION OF THE PREFERRED EMBODIMENTS OF THE INVENTION

Briefly, the present invention in its broadest form is an apparatus and method for detecting flaws in butt welds in steel sheets using horizontal shear ultrasonic waves generated on the surface thereof. Observation of reflected waves having amplitude greater than a chosen value signals the presence of a significant flaw. To achieve this objective, the present apparatus is designed to detect only reflected horizontal shear waves, other modes having been electronically removed using bandpass filters, since they occur at different frequencies. The invention may therefore be used in the presence of surface structures such as clamps and the like, and in the presence of surface nonuniformities in the vicinity of the weld, thereby permitting on-line flaw detection in a steel mill environment without interfering with the line output.

Figure 1:
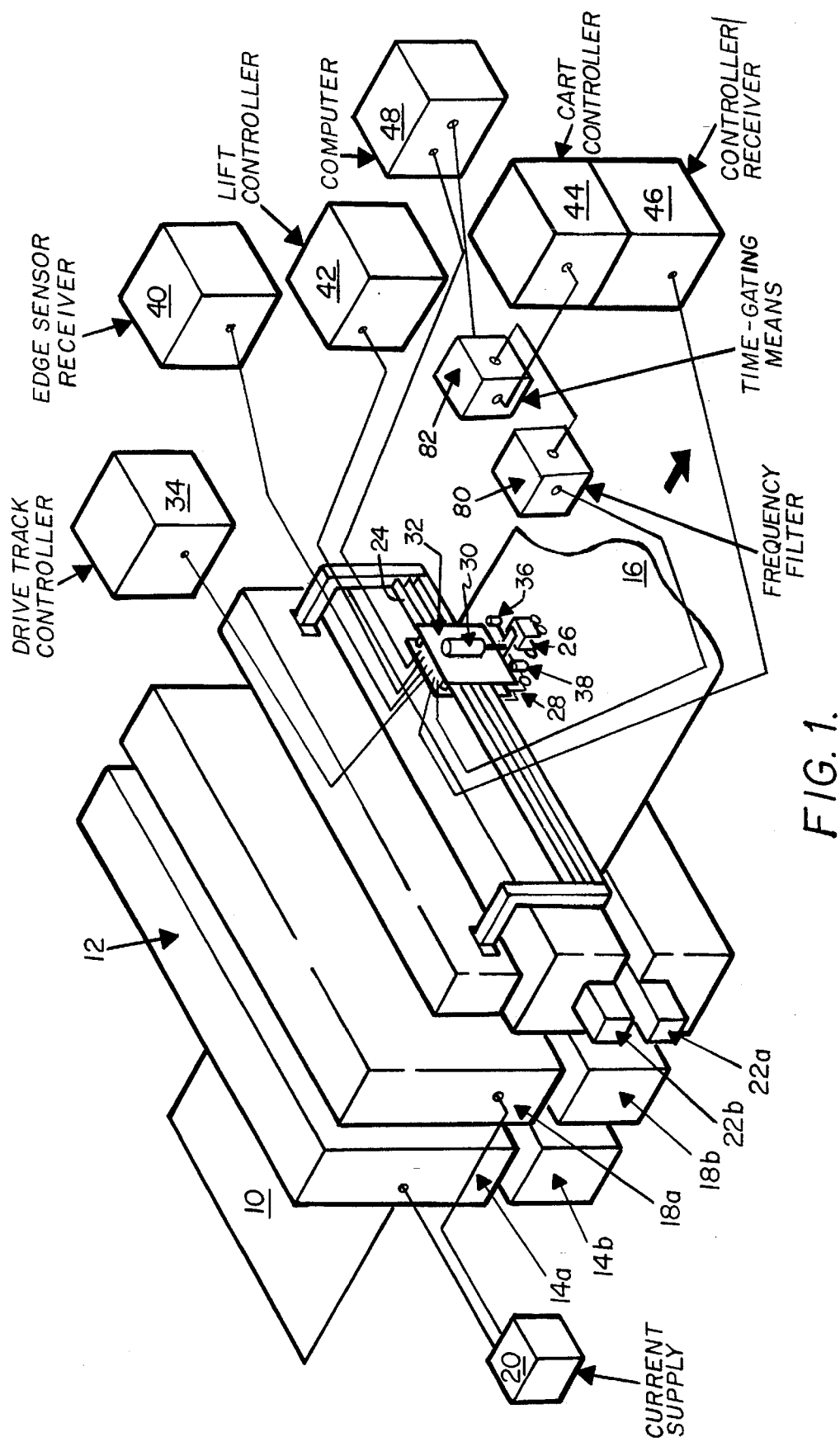
FIG. 1 is a schematic representation of an orthographic projection of the apparatus of the present invention illustrating the utilization of the invention with a common flash butt welder.

Reference will now be made in detail to the present preferred embodiments of the invention, an example of which is illustrated in the accompanying drawings. Identical or similar structure will be identified with identical callouts. FIG. 1 is a schematic representation of the apparatus of the present invention. Steel sheet 10 is fed into the entry end of welder 12, and is clamped by moving platen 14a and 14b. The trailing end of a lengthy steel coil is clamped by fixed platen 18a and 18b. The other end of this sheet and the majority of its length would be located in chemical processing tanks. A weld is achieved by flash butt welder 12 by applying electrical current from supply 20 between moving platen 14a,b and fixed platen 18a,b, and bringing the two sheets into electrical contact. After the weld is completed the steel sheet is advanced to where it is clamped between fixed platen 18a,b and flash trimmer knife clamps 22a, and 22b. A flash trimmer knife (not shown in this Figure) trims the completed weld so that it is generally flat. The flash butt welder so described currently exists in several forms in the steel industry.

As the flash trimmer knife moves across the steel sheet in a transverse direction, the apparatus of the present invention is employed to inspect the weld by following the knife as it proceeds across the weld. Drive track 24 may be attached to the flash trimmer housing of welder 12, as shown in the Figure, or may be free-standing. EMAT carts 26 and 28 are attached to a raising and lowering device 30, which is attached to cart 32 that is driven along drive track 24 by a motor controlled by drive track controller 34. In one embodiment of the present invention, a pneumatic lifter may be employed to lower the EMAT carts onto the steel sheet once they are in a proper position to initiate a scan. Leading edge sensor 36 and trailing edge sensor 38 detect the beginning and end of the steel sheet in the vicinity of the weld, and transmit this information to receiver 40. The leading edge sensor 36 provides a signal when the carts should be lifted at the end of a scan, while edge sensor 38 indicates when the carts are in the proper position to be lowered to initiate a scan. Controller 42 controls lifting device 30. In a preferred embodiment edge sensors 36 and 38 are electric eye sensors. Electric eye sensors may be of the reflective type, where a light beam is reflected from the steel sheet, or of the backlighted type, where a light behind the steel sheet is employed. Clearly, other commonly available apparatus for edge location may be used. These might include ultrasonic radiation, microwave transmission, laser optics, and mechanical means. Transmitter EMAT cart 26 is operated by controller 44, while signals received by EMAT cart 28 are directed to controller/receiver 46. The magnetic fields are al so controlled by controller/receivers 44 and 46. All signals received and controls generated by controllers 34, 40, 42, 44, and 46, are controlled by computer 48, which contains a database including EMAT scan data, weld tracking information such as identification of the steel sheet, date, time, gauge, grade, strip width, and the configuration of the EMAT electronics, as well as all of the appropriate sequencing information for the scans and for control of the flash butt welder and the flash trimmer. Weld rejection criteria is also be included in this database.

Figure 2:
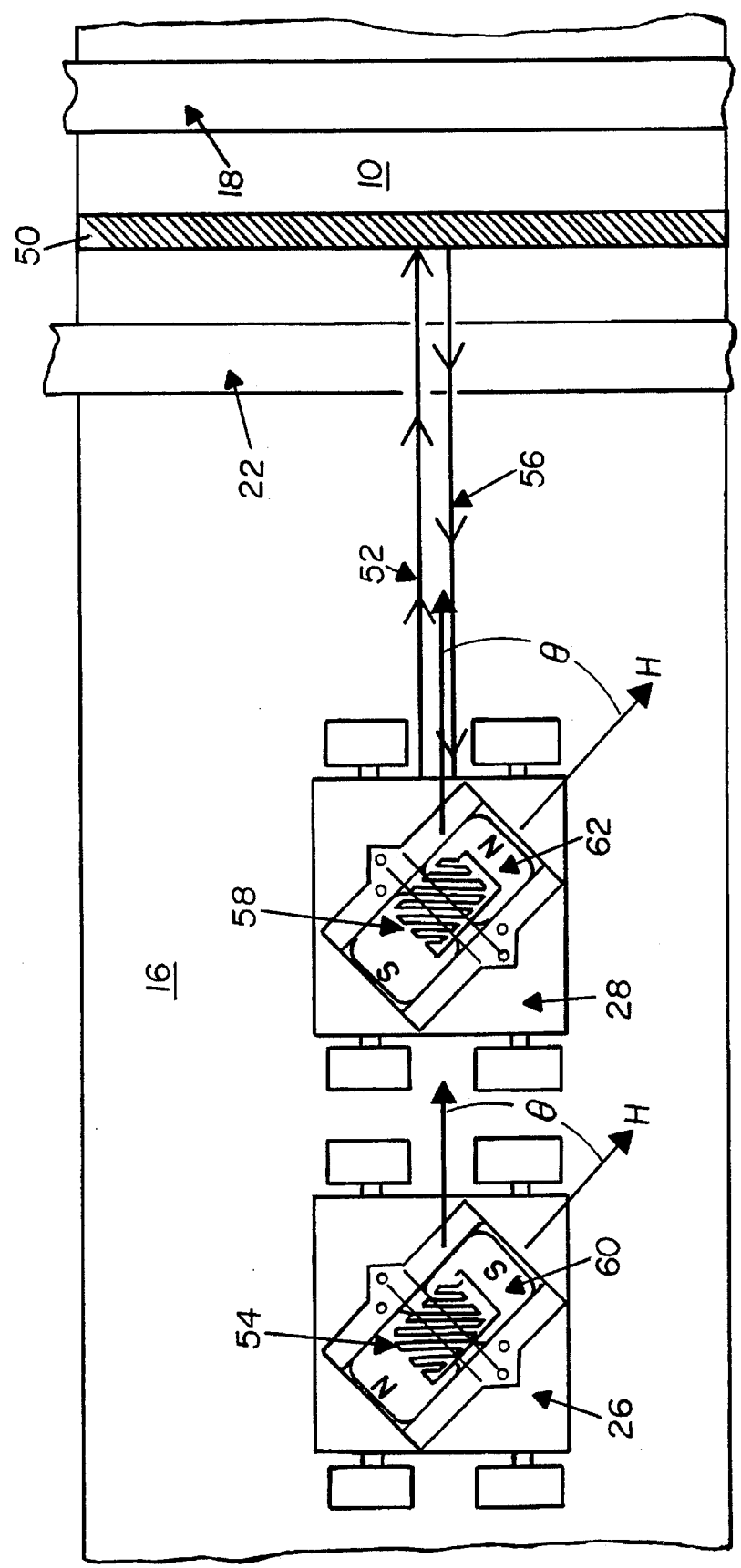
FIG. 2 is a schematic representation of an expanded view of the EMAT carts illustrating the magnets at the "Magic Angle" to the generated horizontal shear ultrasonic wave, and the relationship of the present apparatus to the weld under investigation in the presence of sheet surface clamps.

FIG. 2 is a schematic representation of the top view of the EMAT carts, showing, in particular, the relationship between the carts, the weld, and the trimmer clamps. Horizontal shear- waves 52 are generated by EMAT 54 on cart 26, while reflected ultrasonic shear waves 56 are received and detected by EMAT 58 on cart 28. Magnets 60, and 62 generate magnetic fields designated by H. The "Magic Angle," or angle between the horizontal shear ultrasonic waves generated by EMAT 54 in cart 26 and the magnetic field generated by magnet 60, and the received shear wave 56 and the magnetic field generated by magnet 62, are also illustrated. As shown, carts 26 and 28 are carried by wheels.

In the past, EMATs were oriented either parallel or perpendicular to the magnetic field. As will be discussed hereinbelow, it has been found that at the "Magic Angle," the generation of horizontal shear waves is four times as great as that for the perpendicular or parallel configurations. However, as disclosed in U.S. Pat. No. 4,100,809, supra, at "Magic Angles," $S_0$ and $A_0$ (symmetric and anti-symmetric) vertical shear waves are generated in significant quantities.

Figure 3:
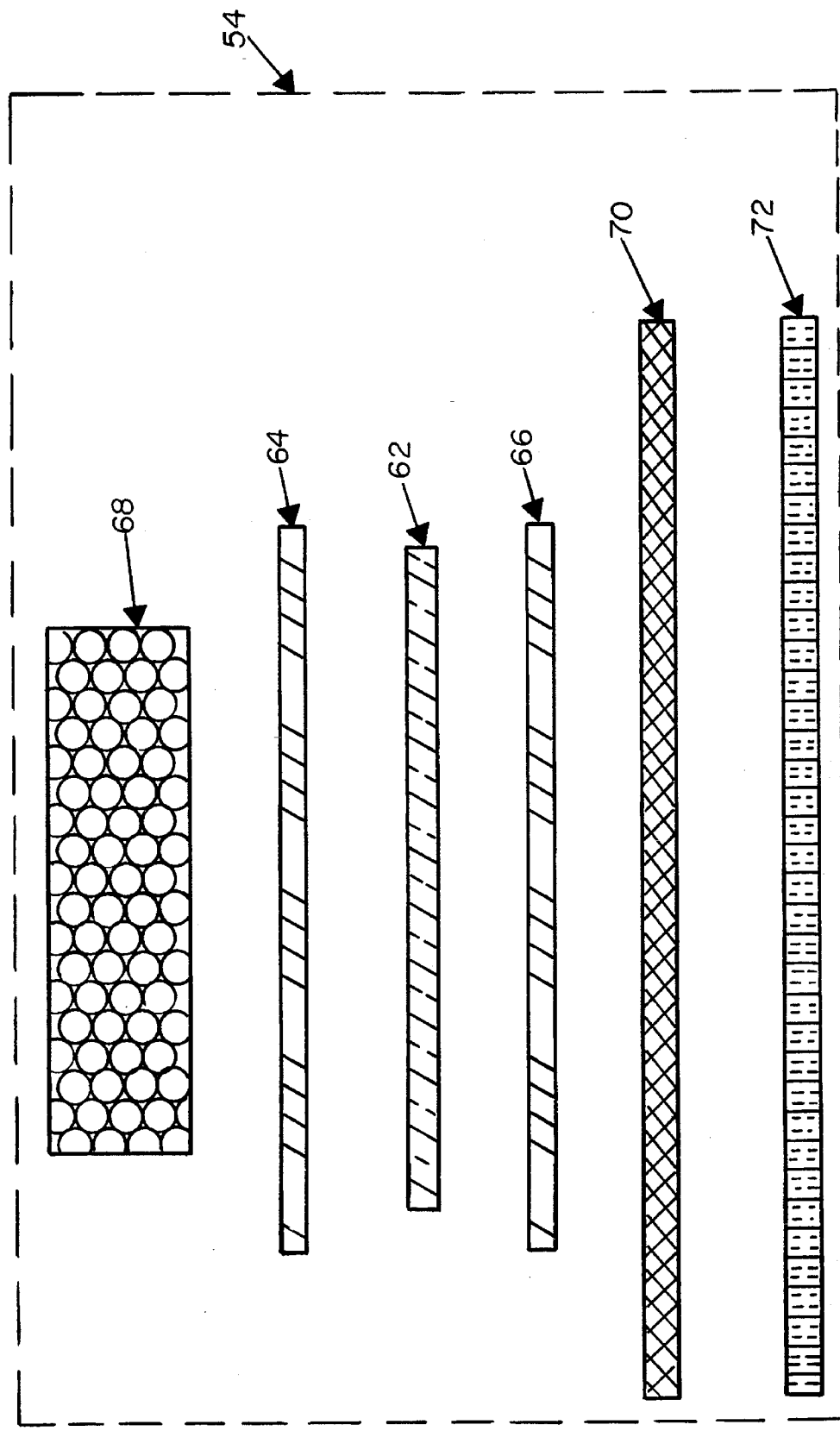
FIG. 3 is a schematic representation of the side view of an EMAT design having a longer wear life than those available commercially and currently employed.
Figure 4A:
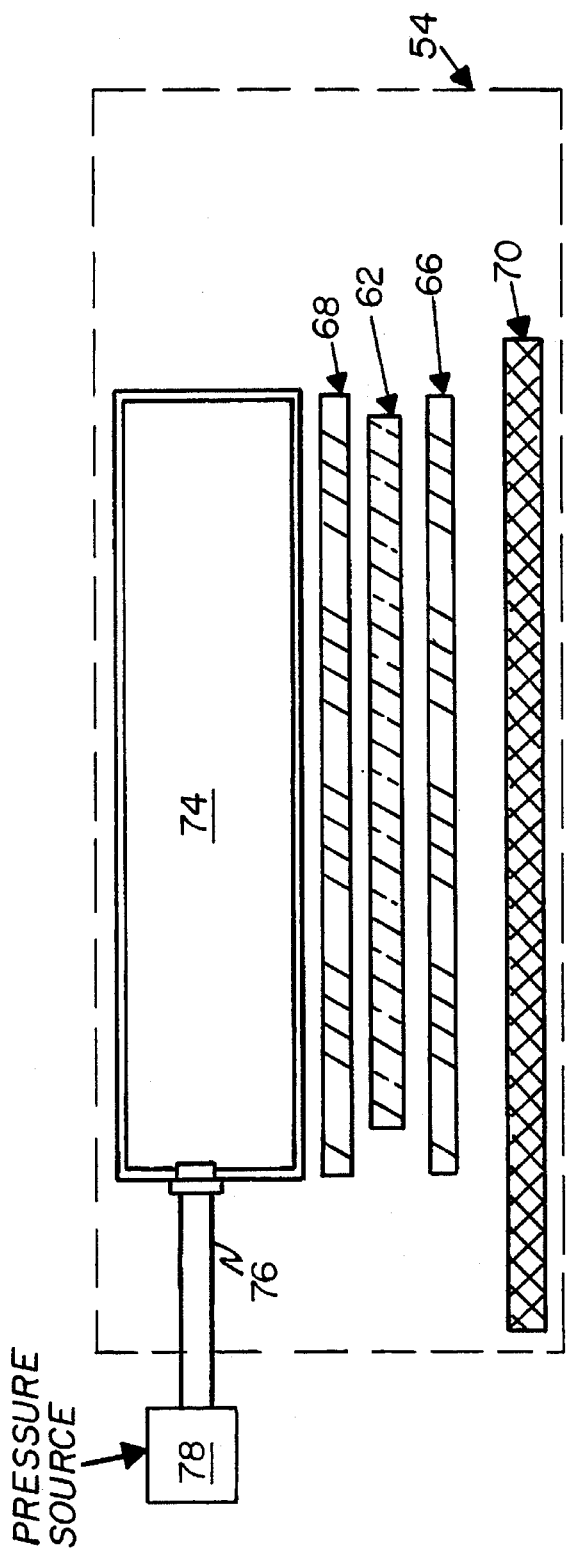
FIGS. 4a and 4b is a schematic representation of another embodiment of an EMAT having a longer wear life than those available commercially and currently employed.
Figure 4B:
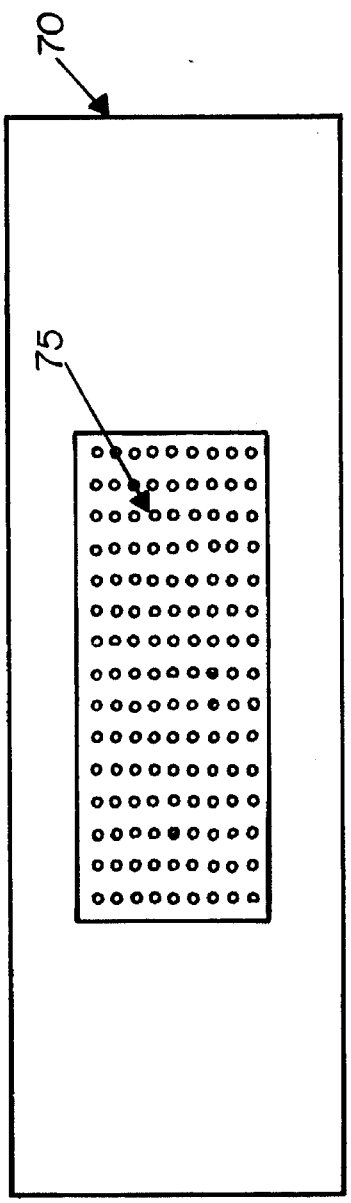

It had been assumed that such angles would not be useful for inspection of butt welds since vertical shear modes would interfere with the flash knife clamps, thereby providing an unacceptable level of noise. FIG. 3 and FIG. 4 illustrate two EMAT designs for extending the wear life of EMATs in industrial environments where EMATs are caused to move against rough, hard surfaces such as steel sheet. Alloys of titanium have been used as a wear surface between the EMAT and the object being tested. Where test objects have smooth surfaces, an ultra-high molecular weight (UHMW) plastic sheet or high temperature teflon, have been employed. However, in the steel mill environment, such plastics have limited use, since they are readily cut and/or punctured by steel shavings on the surface of the sheets. FIG. 3 shows the combination of titanium and UHMW to form the EMAT 54 sliding surface. The EMAT circuit 62 is surrounded, top and bottom, by insulation layers 64 and 66 such as Kapton. Foam layer 68 is used to provide sufficient force on the EMAT circuit in order to keep the circuit and any outer layers close to the steel sheet. Facing the bottom is a layer 70 of an abrasive-resistant material such as titanium, which is bonded to the EMAT circuit layer 62, and the exposed, sliding layer 72, of UHMW plastic. This combination has been found to have a long wear life. The UHMW layer permits the EMAT to slide across the steel sheet, while the metal layer prevents steel shavings from puncturing the EMAT circuit. In the past, such a combination would not have been possible, since EMATs are sensitive to "liftoff" or how close to the surface of the object under investigation is to the EMAT circuit. The signal strength generated by the EMAT at the surface of the material exponentially decreases with the "liftoff" distance. Before "Magic Angles" were utilized, signal strengths were insufficient to permit two layers of surface materials to be used. See, e.g. U.S. Pat. No. 4,295,214, supra, where it is described that by increasing the thickness of the titanium from 0.003 to 0.006 in., the ultrasonic wave generated in the steel sheet was caused to disappear. FIG. 4a is a schematic illustration of another embodiment the extended-life EMAT system of the present invention. Hollow chamber 74 is pressurized using air line 76 from pressure source 78. Molded rubber or phenolic have been employed. Foam layer 68 provides a spring constant to the assembly, and has been described in FIG. 3 hereof. All layers are provided with holes, as illustrated 75 in the outer-metal surface 70 in FIG. 4b, so that the EMAT can be caused to ride on a film of air less than 0. 004 in.

Butt welds must be inspected after the completion of the flash trimming step, since the trimmer knife may introduce flaws into the weld. However, it is known from experience that the weld in the steel sheet is rarely gouged or otherwise damaged by the knife once it has passed the halfway point of the stroke. In order to avoid delays in the steel mill due to weld testing, it is desirable that the EMAT sweep be performed approximately by the time the knife finishes its stroke. Therefore, one begins the inspection process once the knife has traversed past the midpoint of the sheet, moving the EMAT carts at about twice the speed of the knife, behind the knife.

Figure 5:
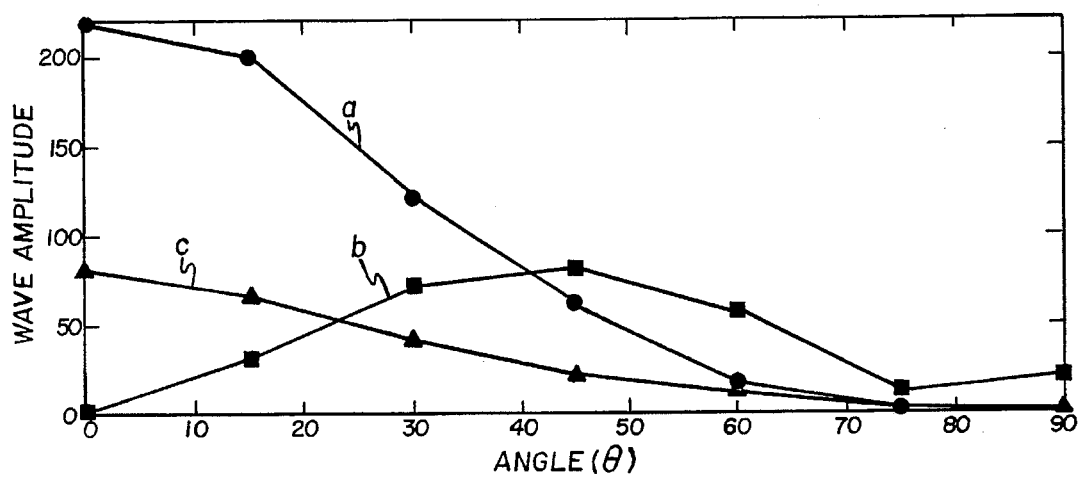
FIG. 5 provides a graphic illustration of the relationship between the angle between the magnetic field and the amplitude of ultrasonic waves generated by the EMAT in the steel sheet for different generated modes.

FIGS. 5–8 provide the experimental and theoretical basis for optimizing the inspection process and apparatus of the present invention. As stated, the horizontal shear wave is the preferred ultrasonic wave mode for the inspection of butt welds so that the waves may pass under the knife clamps without unwanted reflections. FIG. 5 illustrates experimental results for an EMAT having a parallel wire spacing of 0,125 in., which generates an ultrasonic wave having a wavelength of 0.25 in. It is seen that in the 45° to 60° range the SH mode (b) has greater amplitude than the $S_0$ mode (a) or the $A_0$ mode (c), although this result is contrary to theory. It should be pointed out that at 90°, only the SH mode is generated. However, this requires a magnetic field of about 1400 Oersteds as opposed to approximately 350 at 45°. Note also that the wave amplitude at 45° is about four times that at 90°. Thus, although other ultrasonic wave modes are generated in steel sheet at other than 90°, the significant increase in signal strength warrants the use of "Magic Angles," since according to the teachings of the present invention, and as will be discussed hereinbelow, the other modes may be removed by digital or electronic filtering.

Figure 6:
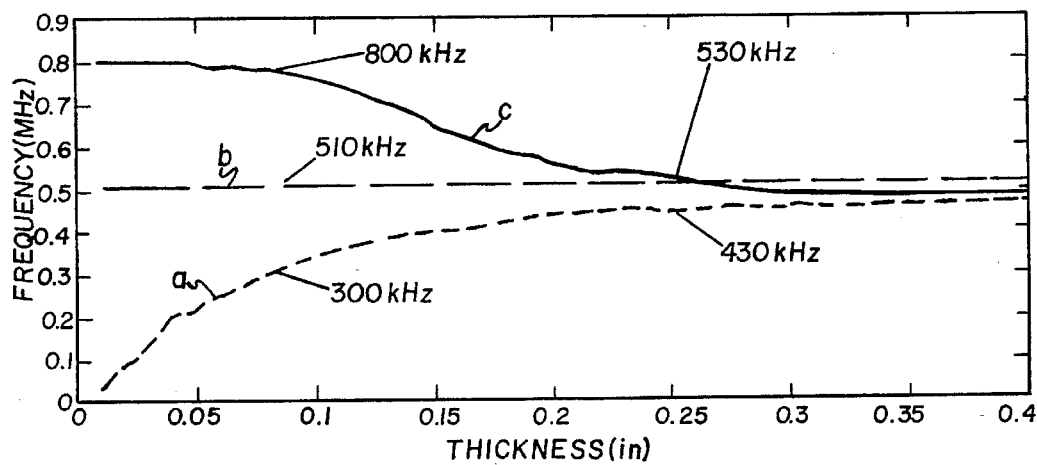
FIG. 6 provides a graphic illustration of the optimum frequency for several modes generated in steel sheets as a function of thickness thereof.
Figure 7:
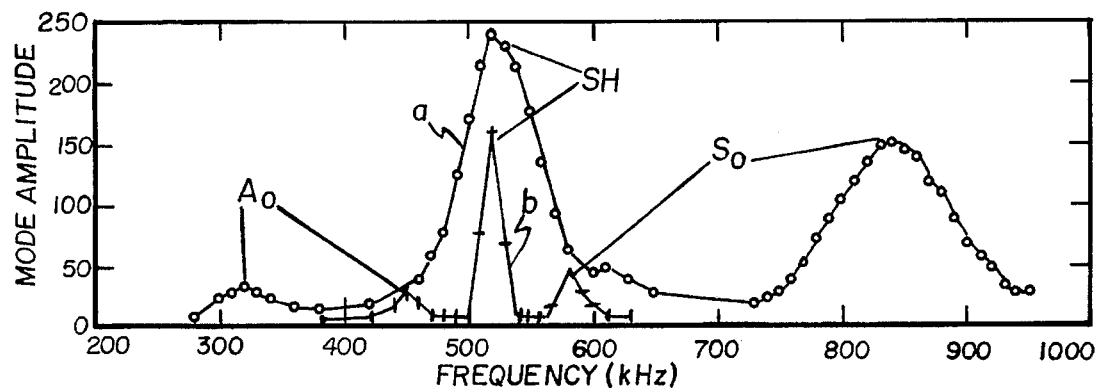
FIG. 7 is another graphic illustration of the fact that each mode h as an optimum frequency in a steel sheet having a particular thickness.
Figure 8:
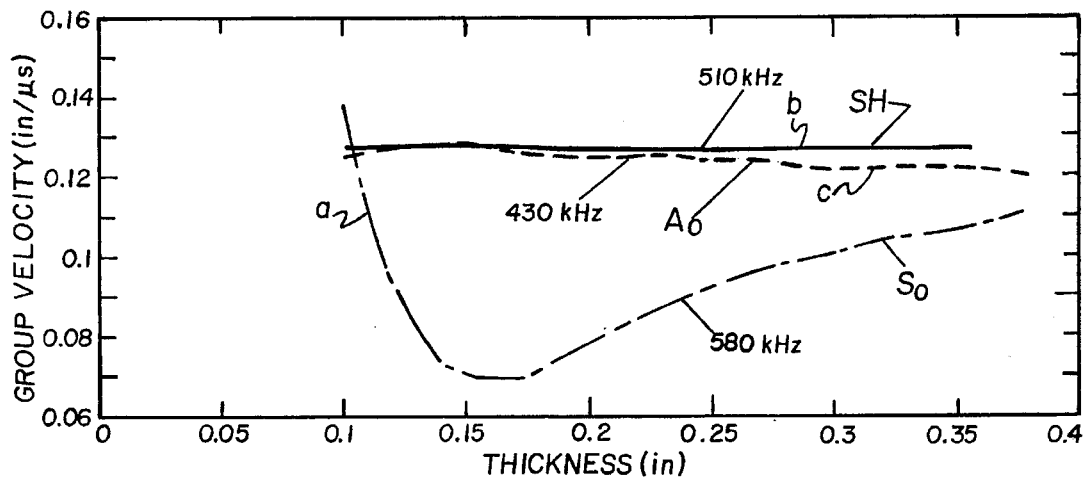
FIG. 8 is a graph of the group velocity of several ultrasonic modes generated in a steel sheet for several sheet thicknesses.

FIG. 6 illustrates the relationship between plate thickness and optimal frequency for ultrasonic waves, for the $S_0$ (a), SH (b), and $A_0$ (c) modes, for a wavelength of 0.25 in. It can be shown that increasing the wavelength increases the frequency separation of the modes at a given wavelength. FIG. 7 illustrates this latter concept for a wavelength of 0.25 in. at two sheet thicknesses, 0.075 in. (a), and 0.25 in.(b), which represent the lower and upper thicknesses commonly processed by steel mills. Clearly, the thinner sheet gives a better mode separation. Of additional interest is the fact that the frequency of the SH mode does not change significantly with plate thickness, and that thinner plates cause the vertical $A_0$ mode to dampen out more quickly than the horizontal modes. FIG. 8 is a plot of the group velocity versus plate thickness for the $S_0$ (a), SH (b), and $A_O$ (c) modes. For thinner plates, the $S_0$ mode has a significantly different group velocity than the other modes. The group velocity correlates with the time of arrival of the echo or reflected pulse. Thus, the $S_0$ mode may be readily removed by time gating the receiving electronics. However, although the $A_0$ mode arrives at about the same time as the SH mode, the amplitude of the $A_0$ mode is considerably smaller than that for the SH mode, and would present only a slight addition to the noise of the detected SH signal. An increase of the wavelength of the EMAT from 0.25 in. to 0.34 in. has been found to improve the frequency separation of the wave modes, especially for thicker sheets.

From the above discussion, a combination of digital or electronic frequency filtering and time-gating the detector electronics readily removes unwanted signals from other than the reflected horizontal shear ultrasonic wave. This is achieved using frequency filter, 80, and time-gating means, 82, as illustrated in FIG.1, hereof.

Calibration and use of the present invention are illustrated in FIGS. 9 and 10 hereof. FIG. 9 shows the electronic signature observed from a reflected SH wave from a 20% flaw depth (0.020 in.) in a 0.10 in. thick steel sheet. In order to calibrate the apparatus, a sample of a weld is cut out of a steel coil and placed in the flash trimmer clamp so that the trimmer knife would travel directly over the weld. Since the distance from the weld to the EMATs is fixed, and the speed of the SH wave in plate steel is a constant independent of sheet thickness, a window representing a time-gate can be placed around the location that an echo from a flaw would be received. For initial window calibration, a clean edge on the steel sheet is used, since this represents a 100% echo from a complete flaw. One also defines the time-gate for the direct-transmitted pulse from the generating P-MAT as it passes under the receiving EMAT on its way to the weld location. By applying this procedure to a number of calibration sheets representing the various products welded in a steel mill, a calibration database can be defined, and the EMATs optimized.

As stated, in the actual pulse echo measurement process, two time-gated signals are recorded. The amplitude of the initial generated SH wave is measured as it passes under the receiving EMAT, and is used to both normalize the subsequently received echo from a weld flaw, and to analyze characterize the condition of the generating EMAT. Flash butt welds typically take about thirty seconds. The cart carrying the EMATs is moved to the edge of the steel sheet during this time period. The weld is then moved to the flash trimmer, where clamps are placed on the sheet. At this point, the edge of the sheet can be located for accurate positioning of the EMATs. This placement is important in order to obtain good reflections from the edges of the sheet. When the trimming knife is about halfway across the sheet, the EMAT carts are lowered to the sheet, and a sequence of ultrasonic SH waves is sent toward the weld as the carts traverse the steel sheet parallel to the weld. The receiving EMAT awaits echoes from flaws in the weld. Since the velocity of SH waves is much greater than the speed of traverse of the EMAT carts, each pulse echo measurement is effectively made by a stationary cart. By adjusting th e pulse rate, or rate at which tonebursts are generated, one can set up the apparatus such that measurements are made at known distances from the starting edge, thereby permitting flaw location to be identified. When the carts approache the far edge of the sheet, it is raised, and the knife clamps released. A computer then analyzes the weld data in order to determine whether any echoes exceed the calibration threshholds or if the integrated area of the detected signals exceeds a preselected value.

FIG. 10a shows a typical display of echoes received from a calibration sheet which contains four flaws; an edge flaw of 0.15, and three flaws of 0.10, 0.15, and 0.25 percent of sheet thickness, respectively. FIG. 10b illustrates the direct transmission signal which is continuously monitored during the measurement in order that the received signal can be normalized. If a weld passes inspection, the mill line sends the sheet forward for further processing. The calibration illustrated in this figure was performed on a 0.10 in. thick steel sheet using 0.34 in. wavelength EMATs. The signals optimized at 350 Gauss pulsed magnetic field at a "Magic Angle" of 45°. The toneburst was 8–12 cycles of a 410 kHz waveform having a maximum peak of 2.2 volts and a 100 Hz repetition rate. The EMAT carts were located about 20 in. from the weld, which is typical in a steel mill.

The foregoing description of several preferred embodiments of the invention has been presented for purposes of illustration and description. It is not intended to be exhaustive or to limit the invention to the precise form disclosed, and obviously many modifications and variations are possible in light of the above teaching. For example, it would be apparent to one having ordinary skill in the art of welding, after studying the present disclosure, that only one EMAT would be necessary to provide the toneburst and receive the reflected signal, if normalized signals were not required. Moreover, under certain situations, the "Magic Angle" might be different for the generating and receiving EMATs. The embodiments were chosen and described in order to best explain the principles of the invention and its practical application to thereby enable others skilled in the art to best utilize in the invention various embodiments and with various modifications as are suited to the particular use contemplated. It is intended that the scope of the invention be defined by the claims appended hereto.

What is claimed is:

1. An apparatus for detecting flaws in butt-welded steel sheet comprising in combination:

a. a first electromagnetic acoustical transducer for generating horizontal shear mode ultrasonic waves in the steel sheet approximately perpendicular to and on one side of the weld;

b. first means for generating a magnetic field parallel to the surface of the sheet and at between 40° and 65 ° to the direction of the horizontal shear mode ultrasonic waves in the vicinity of the generation thereof by said first transducer;

c. a second electromagnetic acoustical transducer for receiving ultrasonic waves in the steel sheet reflected by the weld and for generating an electrical signal responsive thereto, said second transducer being located on the same side of the weld as said first transducer, there being a line formed by the received reflected waves and the generated waves approximately perpendicular to the weld;

d. second means for generating a magnetic field parallel to the surface of the sheet and at between 40° and 65° to the direction of the received horizontal shear mode ultrasonic waves in the vicinity of the reception thereof by said second transducer;

e. means for moving said first transducer and said second transducer across the surface of the steel sheet in a line parallel to the weld;

f. means for receiving the electrical signal from said second transducer and comparing the received signal with that for a weld with acceptable faults; and g. means for removing signals from acoustical wave modes in the steel sheet reflected from the weld other than horizontal shear mode acoustical waves before such signals reach said means for receiving electrical signals from said second transducer.

2. The apparatus as described in claim 1, wherein said means for re moving signals from acoustical wave modes other than horizontal shear mode acoustical waves from said means for receiving electrical signals from said second transducer comprises a band-pass electrical filter chosen to pass electrical signals having frequencies associated with horizontal shear mode acoustical waves.

3. The apparatus as described in claim 1, wherein said means for receiving the electrical signal from said second transducer is time-gated in order to prevent other modes than the horizontal shear mode acoustical waves generated by said first transducer and reflected from the weld from contributing to electrical signals from said second transducer generated in response to horizontal shear mode acoustical waves reflected from the weld.

4. The apparatus as described in claim 1, further comprising means for locating each edge of the steel sheet in the vicinity of the line of traverse of said first transducer and said second transducer across the steel sheet.

5. The apparatus as described in claim 4, further comprising means, responsive to said means for locating each edge of the steel sheet, for placing said first and said second transducer in contact with the surface of the steel sheet in the vicinity of one edge thereof and for withdrawing said first transducer and said second transducer therefrom in the vicinity of the other edge of the steel sheet after said first transducer and said second transducer have been caused to traverse the surface of the steel sheet in a line parallel to the weld by said means for moving said first transducer and said second transducer across the surf ace of the steel sheet.

6. The apparatus as described in claim 1, wherein said second transducer disposed between the weld and said first transducer.

7. A method for detecting flaws in butt-welded steel sheet, comprising the steps of:

a. generating horizontal shear mode ultrasonic waves in the steel sheet approximately perpendicular to and on one side of the weld;

b. generating a magnetic field parallel to the surface of the sheet and at between 40° and 65° to the direction of the horizontal shear mode ultrasonic waves in the vicinity of the generation thereof;

c. receiving ultrasonic waves in the steel sheet reflected by the weld and generating an electrical signal responsive thereto on the same side of the weld as the waves are generated, there being a line formed by the received reflected waves and the generated waves approximately perpendicular to the weld;

d. generating a magnetic field parallel to the surface of the sheet and at between 40° and 65° to the direction of the received horizontal shear mode ultrasonic waves;

e. moving the line of the generated ultrasonic waves across the surface of the steel sheet perpendicular to the weld;

f. removing signals from acoustical wave modes in the steel sheet reflected from the weld other than horizontal shear mode acoustical waves; and g. comparing the generated electrical signal with that for a weld with acceptable faults.

8. The method as described in claim 7, wherein said step of removing signals from acoustical wave modes other than horizontal shear mode acoustical waves is accomplished using a band-pass electrical filter chosen to pass electrical signals having frequencies associated with horizontal shear mode acoustical waves on the generated electrical signal.

9. The method as described in claim 7, further including the step of time-gating the generated electrical signal in order to prevent other modes than the horizontal shear mode acoustical waves reflected from the weld from contributing to the generated electrical signal.

\* \* \* \* \*